(12) United States Patent
Hassingboe et al.

(10) Patent No.: US 9,101,681 B2
(45) Date of Patent: *Aug. 11, 2015

(54) GELATIN NON-WOVEN STRUCTURES PRODUCED BY A NON-TOXIC DRY SOLVENT SPINNING PROCESS

(71) Applicant: Coloplast A/S, Humlebaek (DK)

(72) Inventors: Jens Hassingboe, Graested (DK); Jakob Vange, Helsingoer (DK); Hanne Everland, Bagsvaerd (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/250,419

(22) Filed: Apr. 11, 2014

(65) Prior Publication Data

US 2015/0017862 A1  Jan. 15, 2015

Related U.S. Application Data

(63) Continuation of application No. 12/226,668, filed as application No. PCT/EP2007/053989 on Apr. 24, 2007, now Pat. No. 8,753,672.

(30) Foreign Application Priority Data

Apr. 24, 2006 (DK) .................. 2006 00575
Aug. 21, 2006 (DK) .................. 2006 01090

(51) Int. Cl.

| | |
|---|---|
| B29B 15/00 | (2006.01) |
| B29C 39/14 | (2006.01) |
| B29C 49/00 | (2006.01) |
| B29C 49/08 | (2006.01) |
| B29C 55/00 | (2006.01) |
| B29C 67/20 | (2006.01) |
| B29D 7/00 | (2006.01) |
| B29C 43/22 | (2006.01) |
| B29C 67/00 | (2006.01) |
| A61L 15/32 | (2006.01) |
| A61L 27/22 | (2006.01) |
| D01F 4/00 | (2006.01) |
| D04H 1/42 | (2012.01) |
| D04H 3/073 | (2012.01) |
| D04H 3/12 | (2006.01) |
| D04H 3/16 | (2006.01) |
| D01D 5/04 | (2006.01) |
| D01D 5/14 | (2006.01) |
| A61L 15/42 | (2006.01) |
| B29C 47/00 | (2006.01) |
| D04H 1/00 | (2006.01) |
| D04H 3/00 | (2012.01) |
| D04H 5/00 | (2012.01) |
| D04H 13/00 | (2006.01) |

(52) U.S. Cl.
CPC ................. *A61L 15/32* (2013.01); *A61L 15/42* (2013.01); *A61L 27/222* (2013.01); *B29C 47/0004* (2013.01); *D01D 5/04* (2013.01); *D01D 5/14* (2013.01); *D01F 4/00* (2013.01); *D04H 1/42* (2013.01); *D04H 3/00* (2013.01); *D04H 3/073* (2013.01); *D04H 3/12* (2013.01); *D04H 3/16* (2013.01); *D04H 13/00* (2013.01); *B29K 2089/00* (2013.01); *Y10T 428/2927* (2015.01); *Y10T 428/2933* (2015.01)

(58) Field of Classification Search
CPC ....... A61L 15/32; A61L 27/222; A61L 15/42; D01D 5/04; D01D 5/14; D01F 4/00; D04H 13/00; D04H 1/42; D04H 3/00; D04H 3/073; D04H 3/12; D04H 3/16; B29C 47/0004; B29K 2089/00; Y10T 428/2927
See application file for complete search history.

(56) References Cited

U.S. PATENT DOCUMENTS

| | | | | |
|---|---|---|---|---|
| 3,562,381 | A * | 2/1971 | Sakurada et al. | 264/185 |
| 5,520,916 | A * | 5/1996 | Dorigatti et al. | 424/402 |
| 6,080,420 | A * | 6/2000 | Qin et al. | 424/443 |
| 6,461,628 | B1 * | 10/2002 | Blanchard et al. | 424/402 |
| 8,388,994 | B1 * | 3/2013 | Scheer et al. | 424/423 |
| 8,641,960 | B1 * | 2/2014 | Medeiros et al. | 264/555 |
| 8,753,672 | B2 * | 6/2014 | Hassingboe et al. | 424/445 |
| 2004/0037813 | A1 * | 2/2004 | Simpson et al. | 424/93.7 |
| 2004/0110439 | A1 * | 6/2004 | Chaikof et al. | 442/123 |
| 2005/0073075 | A1 * | 4/2005 | Chu et al. | 264/465 |

OTHER PUBLICATIONS

Xia et al. Tissue Engineering of Cartilage with the Use of Chitosan-Gelatin Complex Scaffolds. Journal of Biomedical Materials Research Part B: Applied Biomaterials. First published online: Jun. 18, 2004. vol. 71B, Issue 2, pp. 373-380.*
Pieper et al. Loading of collagen-heparan sulfate matrices with bFGF promotes angiogenesis and tissue generation in rats. J Biomed Mat Res. 2002, vol. 62, No. 2, pp. 185-194.*
Barbetta et al. Emulsion Templated Scaffolds that Include Gelatin and Glycosaminoglycans. Biomacromolecules. 2008, vol. 9, pp. 2844-2856.*

* cited by examiner

*Primary Examiner* — Marcela M Cordero Garcia
(74) *Attorney, Agent, or Firm* — Coloplast Corp., Coloplast A/S; Nick Baumann

(57) ABSTRACT

The present application discloses an alternative method for the formation of non-woven with fibers in the 1 to 200 μm range. Using an aqueous solution of gelatin (optionally with <30% of low molecular weight alcohol) the fibers are ejected utilizing pressurized air emitted from nozzle and the non-woven formed directly from the emitted thin fibers.

Figure 1:
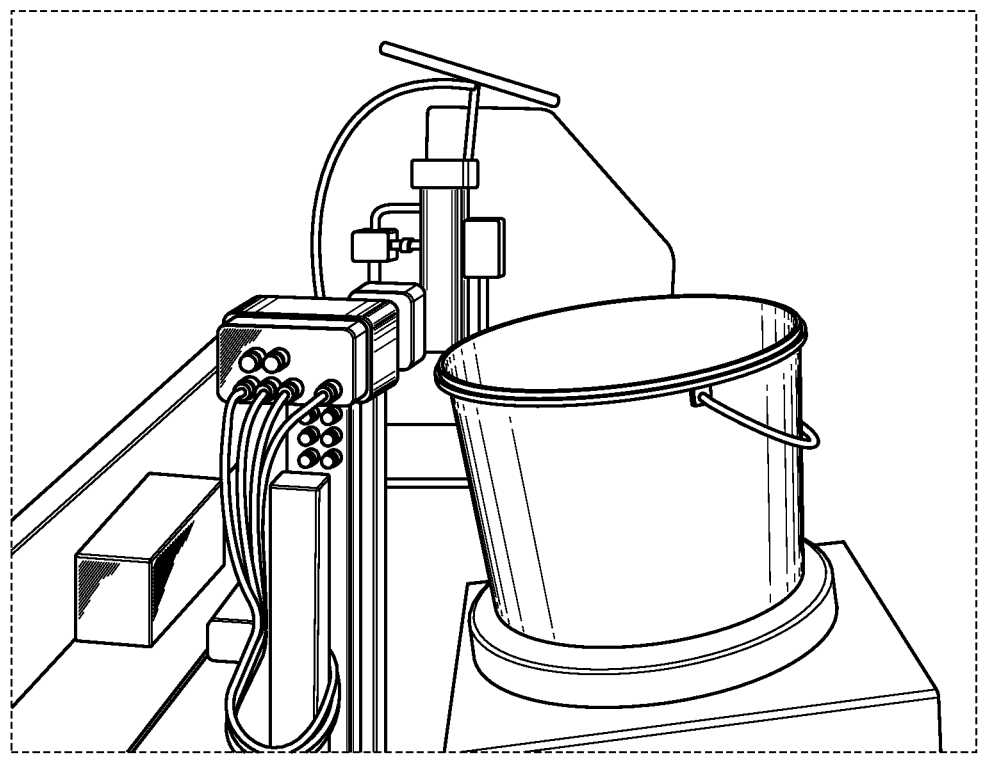

The gelatin non-woven can be cross-linked by heat-treatment or chemical cross-linking, and the non-woven is biocompatible as measured by fibroblast growth in vitro and wound healing on pigs in vivo.

10 Claims, 19 Drawing Sheets

GELATIN NON-WOVEN STRUCTURES PRODUCED BY A NON-TOXIC DRY SOLVENT SPINNING PROCESS

FIELD OF THE INVENTION

The present invention is in the field of production of scaffolds for homeostasis, tissue repair and tissue engineering.

BACKGROUND

Gelatin is prepared by denaturation of collagen. Collagen is a triple stranded helix protein found in skin, cartilage and bones of humans and animals where it serves as a structural component in the extracellular matrices (ECM). The strands found in collagen are in gelatin found as mixtures together with oligomers, breakdowns and other polypeptides forming small local collagen-like triple-helical areas.

The typical sources of gelatin for industrial applications are pigs, cows and fish recovered from collagen by hydrolysis. There are several varieties of gelatin, the composition of which depends on the source of collagen and the hydrolytic treatment used. Type A gelatin results from an acid hydrolysis of typically skin from pigs whereas type B gelatin results from alkaline hydrolysis of cattle hides and bones.

Gelatin has sol gel properties, which are thermo reversible. Above about 37° C. gelatin is in the sol state, whereas below about 37° C. gelatin is in the gel state. The quality of gelatins is commonly characterized by bloom, e.g. according to AOAC standards gelatin bloom test and BS757.

Gelatin is widely applied in pharmaceuticals, foods, medical dressings and technical applications e.g. photographic paper. Due to poor fiber forming properties of gelatin, there are few reports of fibers and non-woven made of pure gelatin and primarily made by electro-spinning using organic solutions (Huang Z M et al. (2004), Polymer 45, 5361-5368) (Zhang et al. (2004) J Biomed Mater Res Part B: Appl Biomater 72B: 156-165). One recent report describes electrospinning of gelatin dissolved solely in water (Li J. et al., Biomacromolecules 2006, 7, 2243-2247). Most often the fiber forming properties of gelatin are improved by addition of another polymer or by grafting or substituting chemical groups to the gelatin chain. Of other examples coating of fibers with gelatin can be mentioned (Lin FH et al. (2000) Materials Chemistry and Physics 64, 1889-195) (W003087444A).

The production of fibers from protein solutions has typically relied upon the use of wet or dry spinning processes (Martin et al. Processing and Characterization of Protein Polymers; McGrath, K. and Kaplan, D., Ed.; Birkhauser: Boston, 1997, pp. 339-370; Hudson, S. M. The Spinning of Silk-like Proteins into Fibers; McGrath, K. and Kaplan, D., Ed.: Birkhauser: Boston, 1997, pp. 313-337).

Wet spinning, more commonly used, involves the extrusion of a protein solution through a spinneret into an acid-salt coagulating bath, which usually contains aqueous ammonium sulfate, acetic acid, isopropanol, or acetone (Nagura et al. (2002) Polymer Journal, Vol 34, No 10, 761-766), (JP2001089929), (Fukae R et al. (2005) Polymer 46, 11193-11194). Alternatively, dry spinning consists of extrusion into an evaporative atmosphere. Both approaches yield large diameter fibers, which do not mimic the morphological characteristics of native collagen fibers. Furthermore, both strategies rely on biologically toxic solvent systems that preclude the fabrication in real time of hybrid protein-cell constructs.

By the electro-spinning process it is possible to make fibers of pure gelatin. E.g. US 2004/0110439 describes durable, load bearing prosthetic materials of cross-linked elastin, cross-linked elastin mimetic protein, cross-linked collagen and/or cross-linked gelatin. Fibers with a diameter in the 200-3,000 nm range are electrospun and a non-woven created.

However the electro-spinning process has low output and relies on the use of expensive and harmful solvents. In wound healing application low density products of gelatin is often made by freeze drying, which has the disadvantage of being a costly process and a batch process.

U.S. Pat. No. 5,017,324 describes the formation of fibers with particles by using one or more spray guns intermixing powder, particulate or strand-like material with the fibrous material to form a non-woven pad.

SUMMARY

The present application discloses an alternative method for the formation of non-woven with fibers in the 1 to 200 μm range. Using an aqueous solution of gelatin (optionally with <30% of low molecular weight alcohol) the fibers are ejected utilizing pressurized air emitted from nozzle and the non-woven formed directly from the emitted thin fibers.

The gelatin non-woven can be cross-linked by heat-treatment or chemical cross-linking, and the non-woven is biocompatible as measured by fibroblast growth in vitro and wound healing on pigs in vivo.

DETAILED DISCLOSURE

A major aspect of the present invention relates to a method of producing fibers of a natural protein structure comprising the steps of:
(a) ejecting an aqueous solution of the natural protein structure through a nozzle, wherein the aqueous solution comprising <25% low molecular weight alcohol; while
(b) emitting pressurized air from air jet bores to attenuate or stretch the natural protein structure fiber; while
(c) collecting the fibers on a collecting device.

The present method allows very thin fibers to be extruded by a method that can be run in commercial scale. The method according to the invention is equally applicable to protein structures that are poor fiber makers as well as naturally fiber forming proteins. Gelatin has low cohesive strength and has been hard to manufacture fibers of. The present technique has proven applicable to make gelatin fibers even from water without the use of organic co-solvents.

Materials applicable to present invention are natural protein structures, alone or in combinations, particular preferred are those originating from the ECM. Examples of such materials are collagen, keratin, fibrin, elastin, laminin, vimentin, vitronectin, reticulin, fibrinogen and derivatives of these and the like found in a native or denaturated form. The viscosity of an aqueous solution of gelatin in the sol state depends on concentration and temperature. In general viscosity decreases with decreasing concentration and decreasing temperature.

In a preferred embodiment of the invention the concentration of a gelatin with bloom strength 300 is from 10% to 60%, but more preferably from 20% to 40%, but even more preferably from 22% to 30%, but most preferably from 24% to 26%. In a preferred embodiment of the invention the viscosity of 25% aqueous solution of a gelatin with bloom 300 is in the range of 1000-2000 mPas at a processing temperature of 40° C. In another preferred embodiment of the invention the viscosity of a 25% aqueous solution of a gelatin with bloom 300 at processing temperatures from 40° C. to 70° C. is in the range of 300-2000 mPas. Processing temperature is preferably below boiling temperature of solvent, e.g. 100° C. of water. In another preferred embodiment viscosity of aqueous solution of a gelatin with bloom 300 in a concentration between 25% and 35% is in the range of 300-8000 mPas at processing temperatures from 40° C. to 70° C. In general a 35% solution of gelatin with bloom 300 needs to be processed at a higher temperature than a 25% solution of same gelatin if viscosity during processing needs to be the same. However processing at higher temperatures will increase the rate by which drying of the formed fiber is taken place. Furthermore in general fiber diameter of the resulting non-woven will be larger when concentration of gelatin is 35% compared to processing a gelatin solution (again with bloom 300) of 25%. Processing of solutions with concentration of gelatin of bloom 300 below 25% is also possible, and in a preferred embodiment concentration is 24% of gelatin (bloom 300). With lower concentrations processing with the described method is also possible, however because viscosity decreases with decreasing concentration the cohesive strength of the solution decreases, hence fiber formation is more difficult. Furthermore the formed non-woven will be wetter, and hence less stable in structure until it is dried. If the non-woven is too wet upon formation it will once it has been dried appear more brittle.

As seen in one of the examples of this patent addition of an alcohol decreases the viscosity of a gelatin solution at least a low temperatures.

It is expected that quality of gelatin, e.g. bloom strength, will influence appropriate processing conditions of the preferred embodiment. Hence when using various qualities of a natural protein, processing conditions such as concentration of spinning solution and processing temperature need to be adjusted in order to obtain preferred embodiment of the described method.

In a preferred embodiment the nozzle has an orifice between 0.008 inch and 0.050 inch, such as bigger than 0.010 inch, and smaller than 0.040 inch, that is smaller than 0.035 inch. Preferably the nozzle has an orifice in the 0.012 inch to 0.030 inch range. 0.030 inch orifice equals a diameter of 762 µm.

To enhance the fiber forming properties of gelatin, and lower the viscosity some solvent is added. However, too much solvent can make the solution sticky and hard to process. It is therefore preferred that the aqueous solution comprises <30% low molecular weight alcohol, such as <25%, or even <10% low molecular weight alcohol (i.e. less than 10% of the final aqueous solution is the solvent). It is even more preferred that the aqueous solution comprises <1% low molecular weight alcohol, that is essentially free from lower molecular weight alcohol. It is also preferred that the aqueous solution is essentially free from any organic solvents.

The low molecular weight alcohol is selected from the group consisting of methanol, ethanol, propanol (1-propanol, 2-propanol), and 1-butanol.

The ejection process takes place when the aqueous solution is ejected as a bead or a droplet.

Non-woven fibrous structures are produced by extruding a material through a nozzle, which due to its structure allows air from nozzles adjacent to the extruding nozzle to enhance the fiber formation by drawing and swirling the material.

The pressurized air is emitted from air jet bores. This attenuates or stretches the natural protein structure fiber by letting pressurized air be ejected from the air jet directed downwardly and substantially tangential to the nozzle (WO94/04282). The air also dries the fibers. Preferably, the pressurized air is blown from a source as close to the orifice as possible, creating a substantially tangentially, downwardly oriented pressurized air flow.

The process and the apparatus is disclosed in detail in WO94/04282.

When the aqueous solution is ejected from the nozzle a thin fiber is formed. Given the high surface area to volume ratio of these fibers, solvent evaporation occurs relatively quickly even when operating with aqueous solutions at ambient temperature and atmospheric pressure. It is appropriate to adjust temperature of both ejected polymer and air such that the formed fibers are dry enough to maintain the formed structure, but not dried too fast. When fibers are not too rapidly dried the gelatin molecules will have time to orient on a molecular level. This is related to the inherent gel-sol properties of gelatin. When subsequent treating the fibers with heat the fibers will cross-link more effectively if the gelatin has been allowed to gel.

The present method avoids the need for biologically toxic solvent systems. Thus, the present process allows real-time fabrication of hybrid protein-cell constructs, and constructs of biologically active constituents: discrete ECM regions.

Gelatin is an example of a poor fiber forming material, which by the described process in this patent can be made into a fibrous non-woven material.

The gelatin fiber is still wet and sticky when it leaves the nozzle. The fiber formation is therefore enhanced if the collection of a fiber is not in a small area, but spread over the collection device. This can be obtained if the fiber ejected from the nozzle hits the collecting device at an angle as described in example 4 where the fibers are sprayed on the inside of an almost vertical rotating cylinder that is close to parallel to the nozzle, or if the collecting device is perpendicular to the nozzle, it has to move at a sufficient speed to spread the fibers. Too slow a speed will result in the fibers sticking together while still wet and forming a more film-like structure.

In one aspect of the invention particles are suspended in the aqueous solution prior to ejection. As the diameter of the nozzle is wider than the diameter of the formed fibers, the particles can have any diameter, up to the diameter of the nozzle, or the particles can be smaller than the diameter of the fibers. Wet, soft, and pliable particles of even larger diameter than the nozzle may be ejected. Thus, in one aspect of the invention the particles suspended in the aqueous solution have a mean diameter wider than the mean diameter of the fibers.

What happens is that the natural protein structure comes out through a somewhat wide nozzle. The width of the nozzles also allows the particle to come through without clogging the nozzle. The thinness of the fibers is obtained through the combination of the air-flow emitted and the consequent stretching the fiber as well as the spinning process forming the non-woven.

Figure 3:
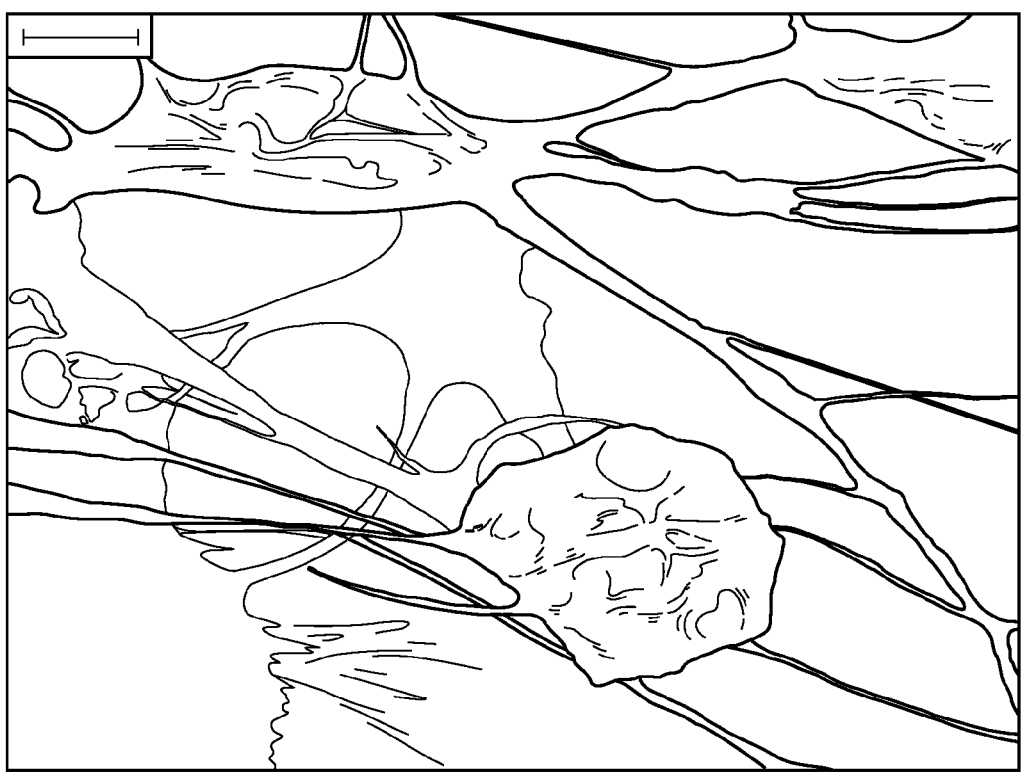

As illustrated in FIG. 3, the thin fiber will have bulbs of particles, where the particles are coated with the natural protein structures. It is preferred that the particles are compatible with the natural protein structures, such that coating is strong. That is, the strength of the fiber will be lowered if the particles are not compatible with the natural protein structures. When the term 'particle' is used, it includes materials in the form of flakes, fibers, particles, powder or the like.

It is preferred that the particles are ExtraCellular Matrix (ECM) particles. ECM is the non-cellular portion of animal or human tissues. The ECM is hence the complex material that surrounds cells. In broad terms there are three major components in ECMs: fibrous elements (particularly collagen, elastin, or reticulin), link proteins (e.g. fibronectin, laminin) and space-filling molecules (usually glycosaminoglycans (GAG's)). ECMs are known to attract cells and to promote cellular proliferation by serving as a reservoir of growth factors and cytokines as well as providing the cells with a scaffold.

The ECM material can be obtained from any mammal. It could be derived from, but not limited to, intestinal tissue, bladders, liver, spleen, stomach, lymph nodes or skin. ECM may be derived from human cadaver skin, porcine urinary bladder submucosa (UBS), porcine urinary bladder matrix (UBM), porcine small intestinal submucosa (SIS).

The active components can also be included in the fiber by dissolving active components in the gelatin solution before spinning. These active components included in the present method can also be, or contain, biological signal molecules e.g. chemo attractants, cytokines and growths factors, polysaccharides, peptides and derivatives of these and the likes. Examples of such materials could be but are not limited to GAG's (chondroitin sulfate, dermatan sulfate, heparan sulfate, hyaluronan, heparin etc.), thrombin, fibrinogen, fibrin, fibronectin, vitronectin, vimentin.

The particles or active components could either consist of one material, cross-linked if necessary, or found in combinations, mixed or cross-linked together.

It is preferred that the method further comprises the step of forming non-woven from the fibers as they are ejected.

The non-woven sheet can be made directly by deposition on a collecting device. The dimension and size of the sheet can be controlled by motion of the collecting device or the extruding device (the nozzle). Endless sheets, which subsequently can be cut into any size or dimension, can also be produced by the method. In fact, it is also possible to make tubular structures. By this process it is possible to make non-woven objects of both well-known fiber forming materials as well as poor fiber forming materials.

It is also preferred that the method further comprises the step of cross-linking the non-woven natural protein structure. Various methods of cross-linking exist like glutaraldehyde or 1-Ethyl-3-[3-dimethylaminopropyl]carbodiimide Hydrochloride (EDC), but in this context it is particularly preferred that the cross-linking is done by heat treatment or ultraviolet irradiation or both. Ultraviolet irradiation can be done as a post treatment or as an in-line continuous treatment. Hereby is avoided to use chemicals that are not compatible with introduction into the body as tissue replacements or with introduction onto the body as dressings.

When using the method for producing gelatin non-woven, the best effect of heat treatment is obtained when the produced gelatin fibers are not dried too rapidly such that sufficient time for gelation, which is an orientation taking place on the molecular level, is ensured. This mean, in essence, that the flow and processing temperatures are adjusted to allow for sufficient slow drying to allow gelation. Non-wovens of gelatin produced and treated this way can be beta sterilized with 25 kGy and still be sufficiently cross-linked. This also applies to other structures made of gelatin for instance by freeze-drying. If the drying of fibers is too rapid cross-linking by subsequent heat treatment will still occur but to a lesser degree. Similarly, cross-linking by heat treatment of freeze dried structures will occur to a lesser degree, if the gelatin solution is not allowed to gel before freezing. One aspect of the invention relates to a process of cross-linking a natural protein structure comprising the step allowing the natural protein to gel prior to drying follow by the step freeze-drying.

Even better cross-linking by subsequent heat treatment can be obtained by adding a polycarboxylic acid to the spinning solution. The benefit is that cross-linking is not taking place in the solution, as will be the case with for example glutaraldehyde. Thus a fiber, a non-woven or for instance a freeze-dried structure can be processed with the cross-linking additive present without activating it. Activation for cross-linking can be done as a simple post treatment neither involving hazardous wet chemistry nor needs for energy consumption due to drying of the product nor induction of deformations of the already obtained structure by for example swelling. Examples of usable polycarboxylic acid are poly acrylic acids, citric acid, and carboxy-methyl-cellulose (CMC) but not excluding others.

In the present context, we understand that a gelatin fiber non-woven is cross-linked if it does not disintegrate or dissolve when submerged in tap water heated above the sol transition state temperature. A simple suggested method is to submerge a uniform integrated gelatin non-woven of 20×20 mm and thickness of 0.5 to 1.5 mm and a weight of 20-30 mg in 38° C. tap water for 2 hours. If it is cross-linked it will be possible to pull the sample up in one piece. If it is not cross-linked it will be dissolved or it will disintegrate when being pulled up.

Suitable crosslinkers are polycarboxylic acids, either the free acid or salts thereof. These could be (but are not limited to): Synthetic: poly(acrylic acid), poly(methacrylic acid), poly(methyl-vinyl ether-co-maleic anhydride) (various grades of Gantrez AN), copolymers of acrylic acid and vinylic monomers (vinylpyrrolidone, alkyl vinyl ethers alkylacrylates, alkylmethacrylates, styrene, maleic anhydride, maleic acid, fumaric acid, hydroxyalkylacrylates, hydroxyalkylmethacrylates), copolymers of methacrylic acid and vinylic monomers (vinylpyrrolidone, alkyl vinyl ethers, alkylacrylates, alkylmethacrylates, styrene, maleic anhydride, maleic acid, fumaric acid, hydroxyalkylacrylates, hydroxyalkylmethacrylates) and copolymers and blends of the above; Natural (acidic polysaccharides most preferred): Pectin, carboxymethylcellulose, sodium alginate, gum arabic, Hyaluronic acid, dermatan sulfate, heparin sulfate, heparan sulfate, chondroitin sulfate and blends of the above.

Crosslinking can be chemical crossbinding, where chemical groups react and form covalent bounds. However, the same effect of stabilization will be obtained when complexes are formed resulting in in-solubility. Such complex formation is also considered crosslinking herein.

The product obtained through this process has several unique properties.

The product preferably has oriented fibers. This is a direct result of a preferred method of the invention, where the fibers are ejected onto a conveyer belt or other moving device. Depending on the speed of the moving device the proportion of fibers in one direction will vary. However, typically the flexibility of a non-woven according to the invention has higher flexibility in one direction than in the other. If this is not a desired feature, the product preferably has two layers with differently oriented fibers.

The product preferably is non-toxic. That is the production process only utilizes a minimum of generally accepted solvents (lower molecular weight alcohols) that evaporates, or at least substantially evaporates, as the natural protein structure is ejected and exposed to the emitted air.

The intended use is a bandage or dressing for human or animal body defects such as wounds or where non-wovens may serve as a useful implant. The use can be as scaffold for tissue repair on the exterior or in the interior of human or animal bodies. The use can be as absorbing device in wounds. Furthermore the use can be structural support inside the body of humans or animals.

The fibers according to the invention will eventually dissolve, degenerate, and degrade when in contact with body fluids. The degeneration rate depends on the body fluid and the degree of cross-linking. This enables the fibers according to the invention to be used as delivery agents, causing controlled release. The substance to be released is preferably added to the aqueous solution prior to ejection. Examples of such substances are peptides, hormones, and vitamins.

One aspect of the invention relates to a non-woven sandwich structure comprising one layer of gelatin with biological active particles on a wound contacting surface of the structure and a second layer of gelatin.

The diameter of the fibers is a consequence of the production process: the air-pressure, the ejection speed, the viscosity of the solution. One aspect of the invention relates to a non-woven with an average fiber diameter of 0.5 and 300 μm, such as 10 to 30 μm. In one aspect none of the fibers have a diameter of less than 0.5 μm and/or more than 300 μm. In another aspect none of the fibers have a diameter of less then 10 μm and/or more than 30 μm. A related aspect relates to a wound dressing comprising non-woven gelatin fibers with a mean diameter of 10 to 30 μm with ECM particles.

One aspect of the invention relates to a non-woven with particles, wherein the average fiber is smaller than the mean diameter of the particles. This is particularly advantageous to combine the flexibility of narrow fibers with the need to incorporate bigger molecules, here exemplified with ECM particles. In one embodiment the average fiber diameter is between 0.5 and 300 μm. In a related embodiment the mean particle diameter is between 10 and 30 μm.

One aspect of the invention relates to a sterilized, cross-linked non-woven of natural protein fibers, such as gelatin fibers. As illustrated in the examples, beta-radiation and/or heat-treatment are suitable for sterilization. As illustrated in the examples heat-treatment optionally in the presence of polycarboxylic acid is suitable for cross-linking.

EXAMPLES

Example 1

Figure 4:
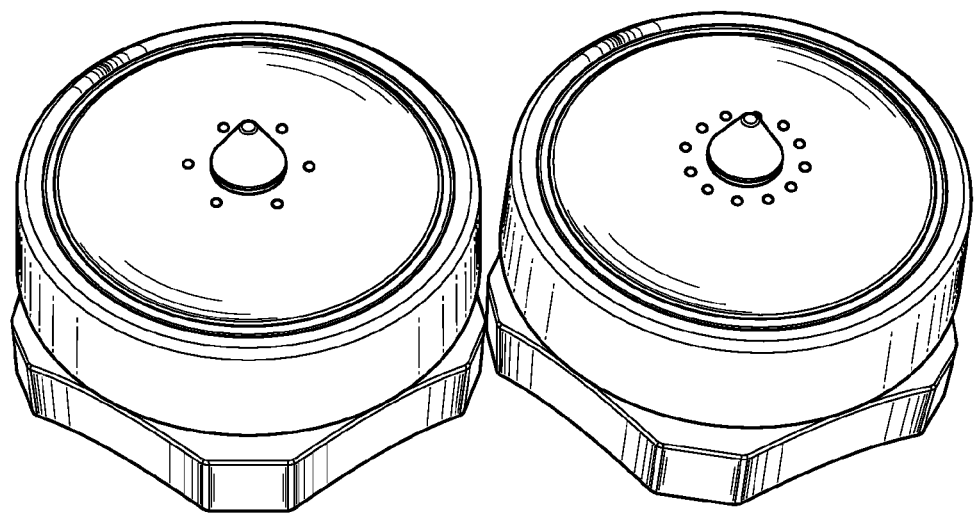

An aqueous solution of type B porcine gelatin with 260 bloom of pharmaceutical grade from Gelita in the ratio of 20 g gelatin to 30 g water and 3 g propanol was prepared. The gelatin was allowed to dissolve in the liquids by heating to 50° C. for several hours. The dissolved gelatin solution was transferred to a can, which fit a small lab-size bulk melter built especially for this purpose. The size of the can used with the bulk melter is approximately from 0.5 liter to 1 liter. The bulk melter heats only the upper surface of the material in the can, which then becomes a viscous liquid and therefore can be pumped to a dispensing unit, mounted hereto. The dispensing unit is a CF-200 Controlled Fiberization Gun provided from Nordson Corp, equipped with a nozzle with 0.012 inch orifice and 6 air holes (FIG. 4). The temperature of the bulk melter can be controlled in its different parts. The temperature of the gun can be controlled and the temperature and rate of the air is controlled.

The temperature of the gelatin was kept at approx. 50° C. and the air was not heated. The obtained non-woven was rigid and the resulting fibers had a diameter from 100 to 200 μm.

The air-flow is controlled by a valve. A maximum of approximately 20 l atmospheric air per min is used.

Example 2

In a setup similar to the one described in example 1 a nozzle with an orifice of 0.030 inch (6 air holes) was used. The obtained non-woven was similar in structure to the one described in example 1.

Example 3

In a setup similar to the one described in example 1 the temperature of the gelatin was kept at approximately 92° C., and the air was heated to approximately 92° C. The obtained non-woven was less rigid than in example 1 and fibers were approximately 100 μm wide. A similar result was obtained using a nozzle with an orifice of 0.030 inch.

Example 4

Figure 5:
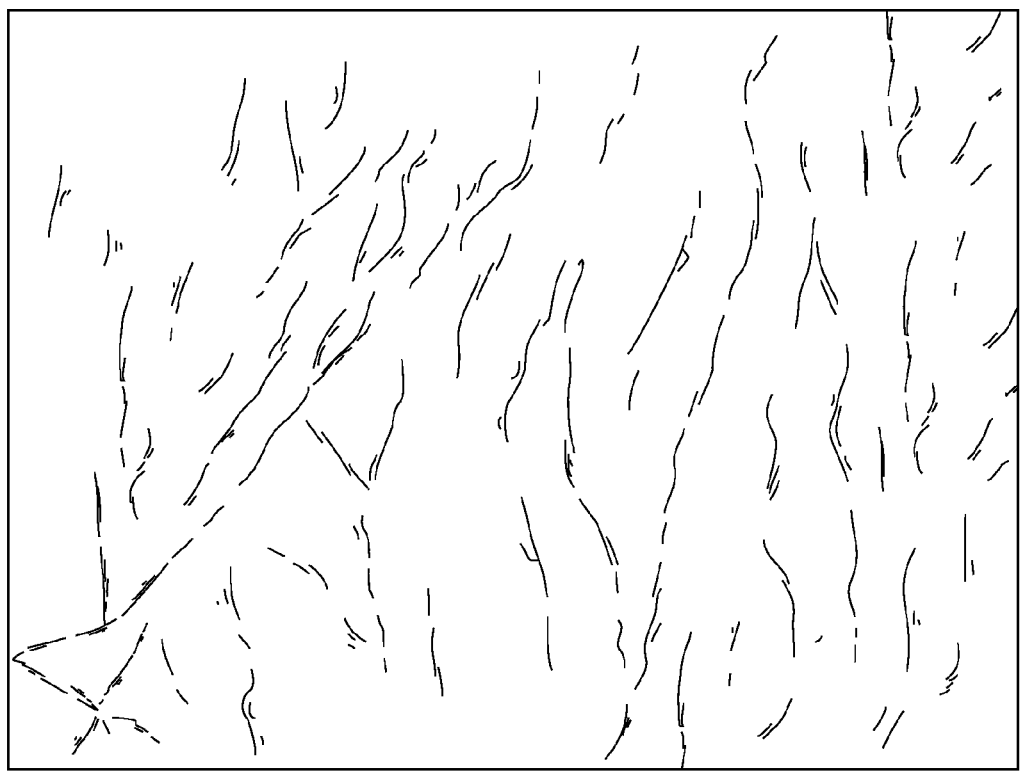

An aqueous solution of porcine gelatin with bloom 300 from Gelita was prepared similar to example 1. The solution contained 30% gelatin and 5% propanol. A nozzle with an orifice of 0.018 inch was used with the equipment mentioned in example 1. A fibrous non-woven structure could be obtained when the collecting device was held in a parallel position to the fiber extruding direction. It was found that an easy way to process a non-woven sheet was when a rotating cylinder was used as a collecting device (FIG. 1). In this case the non-woven sheet was collected on the inner vertical surface of the rotating cylinder. While the cylinder was rotating it was furthermore moved in the vertical direction alternating from an upward movement to a downward movement. When a constant rate of the movements of the collecting device was maintained and the rate of fiber output was kept constant it was possible to create a non-woven sheet, which has a uniform appearance (FIG. 5).

The powerfulness of this process is seen by the fact that in approximately 5 minutes a non-woven gelatin with an area of app. 1350 cm$^2$ and an approximate thickness of app. 2 mm is made.

Example 5

Figure 2:
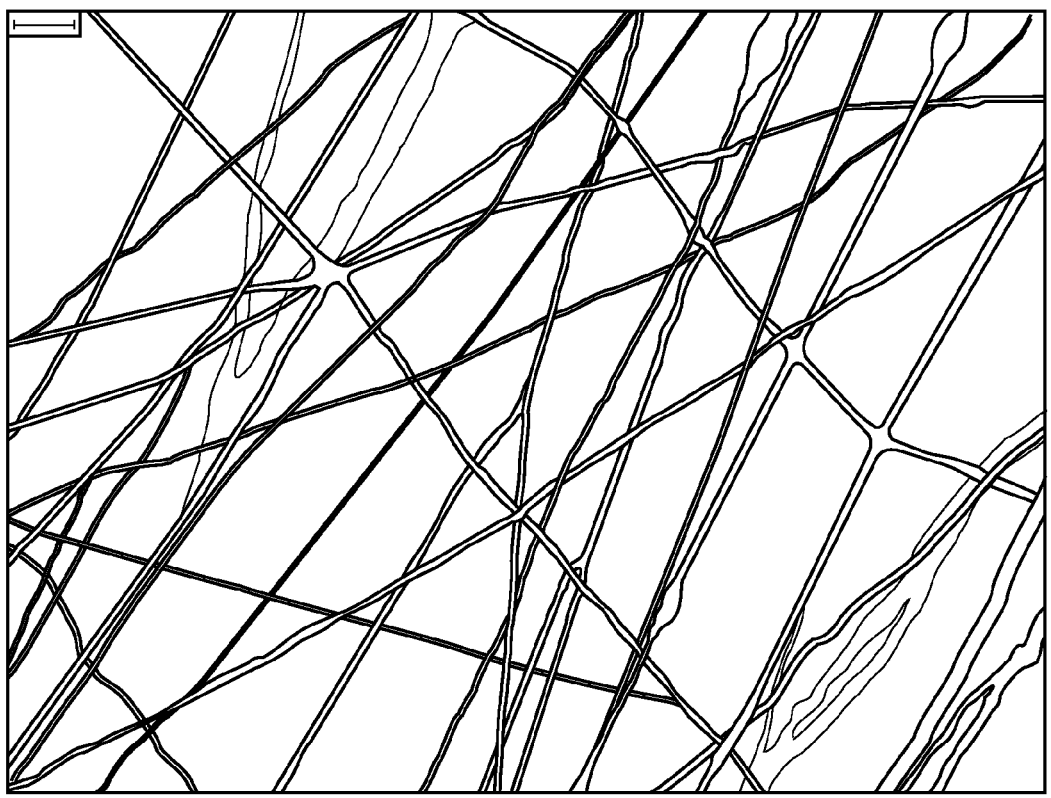

In another experiment similar to example 4 a 30% gelatin solution was made in pure water (70%) without alcohol. The fibers of the resulting non-woven had diameters from 3 to 7 μm (FIG. 2).

Example 6

In another experiment similar to example 5 a 35% gelatin solution was made. The fibers of the resulting non-woven had diameters from app. 4 to app. 17 μm with an average of app. 9 μm. The non-woven was cross-linked by a heat-treatment. The heat-treatment was done over night in a vacuum oven, which upon evacuation of air was heated to 120° C. The cross-linked fibers swell upon hydration but do not dissolve, which on the other hand was seen with untreated gelatin non-woven.

To evaluate the cell morphology and 3D growth of fibroblasts on gelatin fibers, biopsies were punched out and seeded with primary human fibroblasts (passage 3) on the surface with a density of $2.5 \times 10^4$ cells/cm$^2$ in a small volume of growth medium (10% FCS in DMEM) containing antibiotics (penicillin, streptomycin and Amphotericin B). The scaffolds were incubated at 37° C. at 5% $CO_2$ before additional growth medium was added. Evaluation of the cells attachment, morphology, growth and population of the scaffold were performed on day 1, 3 and 7 by staining the cells with neutral red followed by evaluation using an Leica DMIRE2 inverted microscope fitted with a Evolution MP cooled colour camera (Media Cybernetics). Digital images were taken using Image Pro Plus 5.1 software (Media Cybernetics).

The fibroblasts were adhering to the fibers as spindle-shaped cells growing on single fibers except in regions where several fibers were crossing each other. These cells were growing across the fibers. There was a continuous increase in cells number from the start of the study at day 1 to day 7.

Example 7

In another experiment with a setup similar to the one described in example 6 a 24% gelatin solution was used. In the gelatin solution particles of porcine urinary bladder matrix (UBM) was mixed in. The dry matter of the UBM particles was 30% of the dry matter of gelatin. The average particle size of the particles was approximately 150 µm. A nozzle with an orifice of 0.030 inch was used. The fibers were cross-linked by a heat-treatment similar to the one described in example 6. The resulting non-woven had fibers with diameter from app. 3 µm to app. 15 µm with an average of app. 7 µm (FIG. 3).

In order to evaluate the cell morphology and 3D growth of fibroblasts on gelatin fibers+/−UBM particles, biopsies were punched out of each type of the scaffolds and seeded with primary human fibroblasts (passage 3) on the surface with a density of $2.5 \times 10^4$ cells/cm$^2$ in a small volume of growth medium (10% FCS in DMEM) containing antibiotics (penicillin, streptomycin and Amphotericin B). The scaffolds were incubated at 37° C. at 5% $CO_2$ before additional growth medium was added. Evaluation of the cells attachment, morphology, growth and population of the scaffold were performed on day 1, 3 and 7 by staining the cells with neutral red followed by evaluation using an Leica DMIRE2 inverted microscope fitted with a Evolution MP cooled colour camera (Media Cybernetics). Digital images were taken using Image Pro Plus 5.1 software (Media Cybernetics).

The cell growth showed on both types of gelatin fibers (+/−UBM particles) and on all days tested adherent cells growing as spindle-shaped cells. The cells were growing around the fibers and in areas where several fibers were crossing each other the cells were stretching across the fibers. At the first days of the study no difference was seen between having UBM particles in the scaffold or not but at day 7 it was apparent that the cells were more dispersed in the scaffold containing UBM particles compared to the pure scaffold and also contracted this scaffolds more. There were a continuously increase in cells number from day 1 and to day 7.

One large SPF pig (crossbred of Durac, Yorkshire and Danish landrace at Lab Scantox, Denmark) had circular full-thickness wounds approximately 20 mm in diameter. The non-woven with UBM (20 mm disc), tested in duplicates, was carefully applied on top of the wound-bed. To obtain optimal contact to the wound-bed, each material was held in place by a 20 mm pre-wetted foam plug and covered by foam dressings. On day 2 the top-foam dressing was removed and the foam plug was very carefully removed, so as not to disturb the healing and to ensure that the sample materials remain in full contact with the wound bed. The wounds were covered by a hydrocolloid dressing (Comfeel Plus) and changed on day 3, 6, 8, 10, 12 and 15. Following euthanasia, each wound was cut free as a block separated from skeletal muscle tissue and fixed in 10% neutral buffered formalin. The fixed samples were paraffin embedded and sectioned in 5 µm slices stained with haematoxylin and eosin (HE) for general structure of tissue, Masson's trichroma for newly formed collagen and von Willebrand factor for angiogenesis. The evaluation was performed by a trained pathologist at Lab Scantox.

Massive amounts of granulation tissue developed was observed consisting mainly of large numbers of thin-walled blood vessels and fibrocytes/fibroblasts (fibrovascular connective tissue). Moderate amounts of newly formed collagen and slight angiogenesis were present in the wounds. A minimal presence of foreign material likely to be test item was recorded and minimal numbers of clear vacuoles were observed in the profound granulation tissue.

In the superficial parts of the wounds a moderate to marked inflammation was found. In the deeper parts of the wounds a marked inflammation was present. Marked numbers of giant cells were seen and minimal to slight haemorrhage was recorded.

The re-epithelialisation was slight and the thickness of the epithelium was marked in some cases with rete-ridge formation.

In conclusion, no significantly difference in the histopathological wound healings parameters assessed were detected between the non-wowen and the untreated control wounds. However a tendency towards more giant cells were seen in the treated wounds compared to control wounds, probably reflecting a foreign reaction to the non-woven, a common and naturally reaction to materials left in wounds.

Example 8

It was tested whether it was possible to cross-link the gelatin non-woven by a heat-treatment, which do not involve vacuum. A one hour treatment at 160° C. was performed at either atmospheric pressure or in vacuum (created with an oil pump—the pressure of the setup (oven, tubes, device for precipitating volatiles by freezing) was later measured to decrease below 0.01 mBar. This level is reached after approximately 30 minutes). Gelatin non-wovens made similar to the description in example 5 were conditioned to different moisture contents before cross-linking treatment. The moisture contents were measured with Karl Fischer titration. The degree of cross-linking was measured with a protein assay using a bicinchoninic acid kit for protein determination (Sigma BCA-1), where the percent of not cross-linked gelatin was evaluated against a standard curve. Untreated fibers (no heat no vacuum) have percentages of not cross-linked protein of above 100%.

TABLE 1

Percent of not cross-linked protein in gelatin non-wovens with different initial moisture contents heat-treated for 1 hour at 160° C. in vacuum oven or conventional oven. Untreated non-woven has percentages above 100.

| Moisture content | Vacuum oven | Conventional oven |
| --- | --- | --- |
| 5% | 30 ± 2 | 47 ± 7 |
| 8% | 28 ± 2 | 41 ± 2 |
| 20% | 30 ± 3 | 40 ± 1 |

The results shown in Table 1 demonstrate that heat-treatment under vacuum is more effective towards cross-linking than heat-treatment at ambient pressure. Furthermore initial moisture content has no influence on the degree of cross-linking Example 9

The following different mixtures (% of weight) were tested using a 300 bloom porcine gelatin from Gelita:

| Sample | Gelatin | water | solvent |
|---|---|---|---|
| a) | 60.2% | 36.2% | 3.6% 1-propanol |
| b) | 60% | 32% | 8% ethanol |
| c) | 50% | 45% | 5% 1-propanol |
| d) | 50% | 40% | 10% 1-propanol |
| e) | 30% | 60% | 10% 1-propanol |
| f) | 40% | 52% | 8% 1-propanol |
| g) | 40% | 52% | 8% ethanol |
| h) | 40% | 52% | 8% 2-propanol |
| i) | 40% | 52% | 8% 1-butanol |
| j) | 37% | 48% | 15% 1-propanol |
| k) | 37% | 48% | 15% ethanol |
| l) | 34.5% | 43.5% | 22% ethanol |
| m) | 35% | 62.5% | 2.5% 1-propanol |
| n) | 35% | 60% | 5% 1-propanol |
| o) | 35% | 57.5% | 7.5% 1-propanol |
| p) | 35% | 55% | 10% 1-propanol |

The conclusion from the fiber drawing experiments done with the different mixtures is that an alcohol enhances the fiber forming properties of gelatin, and lowers the viscosity. 1-propanol works best. On the other hand the gelatin solution becomes stickier by addition of an alcohol. From a practical point of view the enhanced stickiness is less desirable with the given laboratory equipment, because problems with stopping of the nozzle occur more often. This means that although fiber can be made the process is not running stable over a longer time period (with the given equipment), but maybe only for a few minutes and in some cases less than a minute.

Example 10

Using the same equipment as described in the previous examples a 30% gelatin with 10% 1-propanol was made into a non-woven. The extruding unit was kept at a temperature of 92° C. and the air was cooled to −4° C. The collecting device was a hollow metal plate cooled to negative temperatures by placing dry ice in the interior hollow space of the metal plate. The non-woven was subsequently transferred to a desiccator in order to dry the non-woven. The obtained structure was less fleece-like and more compact like a film compared to the non-woven described in example 4, 5, and 6.

Example 11

Example of a two-layered non-woven construct: Gelatin with biological active particles can be deposited first on the collecting device as a layer of fibrous non-woven and subsequently a layer of pure gelatin can be deposited on the collecting device, on top of the first layer. The benefit of this construct is that it can be placed in a wound such that the layer containing biological active particles is placed closest to the wound surface and the second layer of gelatin serves as an absorbing layer.

Example 12

Figure 6:
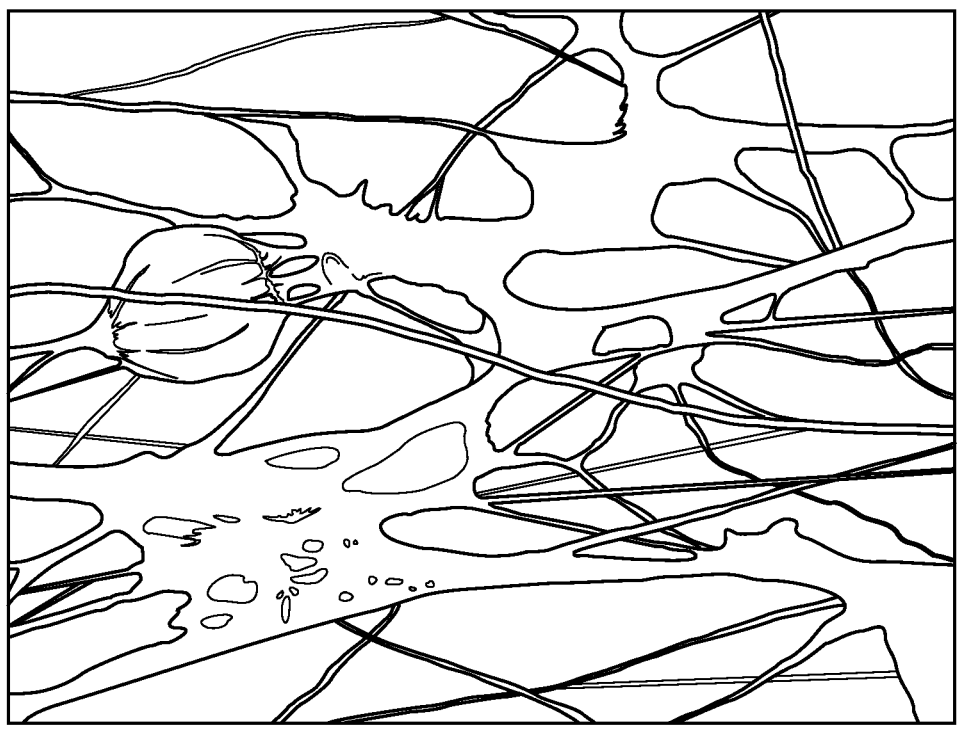
Figure 7:
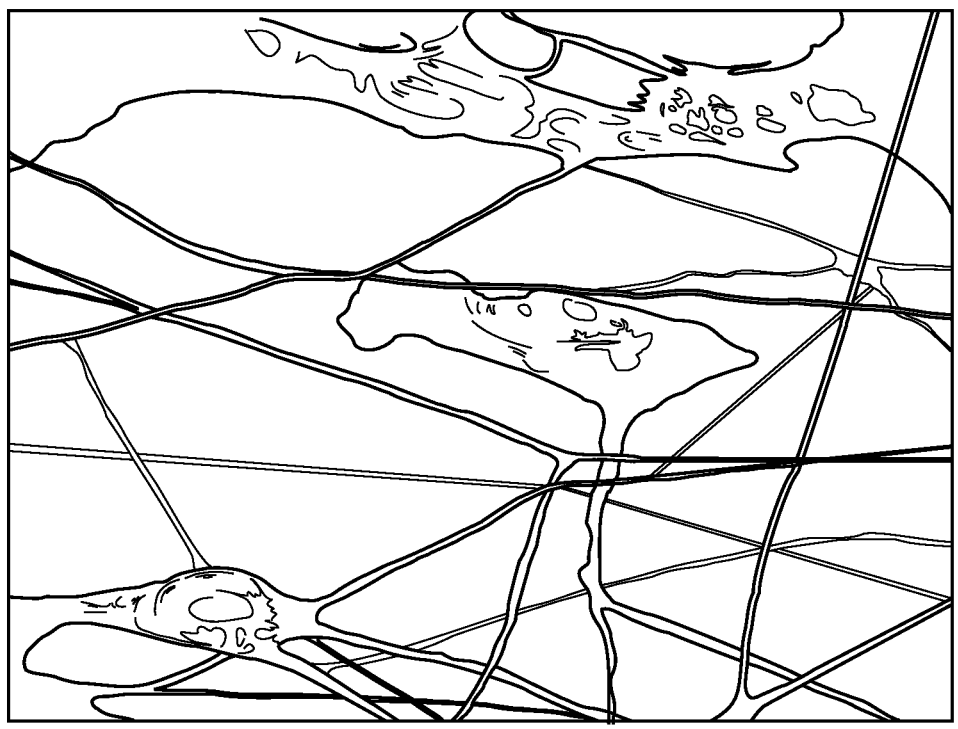
Figure 8:

Gelatin non-woven was made using the equipment described in example 4. The following samples were prepared: pure gelatin (K), gelatin with Esacure (E), and gelatin with ascorbic acid and riboflavin (V). The aqueous solution consisted of 24% dry matter gelatin (porchine bloom 300 from Gelita) with 0.8% of dry matter of Esacure (32% active), which is an ultraviolet curing photoinitiator supplied by Lamberti spa. Other non-wovens were made similarly but with an aqueous solution of 24% gelatin with 0.24% ascorbic acid and 0.24% riboflavin (C, and $B_2$ vitamin). Non-wovens of pure gelatin were made similarly. The samples were processed in order to have approximately similar fiber thickness and non-woven thickness (FIGS. 6, 7 and 8).

The dissolved gelatin solution was transferred to a can (1 Liter), which fit a small lab-size bulk melter (example 4). The bulk melter heats only the upper surface of the material in the can, which then becomes viscous and therefore can be pumped to a dispensing unit, mounted hereto. The dispensing unit is a CF-200 Controlled Fiberization Gun provided from Nordson Corp, equipped with a nozzle with 0.012 inch orifice and 6 air holes. The temperature of the bulk melter can be controlled in its different parts. The temperature of the gun can be controlled and the temperature and rate of the air is controlled. The pump was set at 1. Air pressure was 1.4 to 1.6 bar, and temperature of air was 70° C. (K), 75-80° C. (E), 50° C. (V). A fibrous non-woven structure could be obtained when the collecting device was held in a parallel position to the fiber extruding direction. It was found that an easy way to process a non-woven sheet was when a rotating cylinder was used as a collecting device. In this case the non-woven sheet was collected on the inner vertical surface of the rotating cylinder. While the cylinder was rotating it was furthermore moved in the vertical direction alternating from an upward movement to a downward movement. When a constant rate of the movements of the collecting device was maintained and the rate of fiber output was kept constant it was possible to create a non-woven sheet, which has a uniform appearance.

Samples of the three different non-woven fibers were given ultraviolet irradiation (A FusionI600 H-tube lamp was used for the UV treatments. The distance from lamp to samples was approximately 30 cm). Two intensities, 40% and 100%, were applied for either 30 or 180 seconds. In order to test the degree of cross-linking the samples were immersed in PBS buffer at ambient conditions. Untreated samples of all three non-woven (Esacure, $B_2$C-vit and control) dissolved during few hours. UV-treated gelatin non-woven containing Esacure remained intact with visible fibers after four days. UV-treated gelatin non-woven containing $B_2$C-vitamin also cross-linked but to a lesser degree than the samples containing Esacure. The UV-treated control fibers did not dissolved after 4 day but gelled and thus a cross-linking effect of UV was clearly seen as well. In this experiment the less harsh UV treatments, i.e. the 40% intensity for 30 s or 180 s, seemed to give better cross-linking than the other treatment. Thus 100% intensity for 180 s is too harsh.

In a second experiment the following 10 combinations of 3 treatments were given to the K, E and V samples.

The three treatments were:
Heat: one hour at 160° C. under vacuum
UV: 180 seconds at 40% intensity of the UV lamp
Beta: sterilization by beta-irradiation with a dose of 25 kGy
The 10 combinations were:

| | |
|---|---|
| 1 | Untreated control |
| 2 | Beta |
| 3 | Heat |
| 4 | UV |
| 5 | Heat, Beta |
| 6 | UV, Beta |
| 7 | Heat, UV (first heat then UV) |
| 8 | UV, Heat (first UV then heat) |
| 9 | Heat, UV, Beta |
| 10 | UV, Heat, Beta |

The degree of cross-linking of the 30 different samples were examined by BCA protein assay with four replicates of each sample.

TABLE 2

BCA protein assay—a value of 100 means that
100% of the sample is not cross-linked. Thus a
low number is preferable in terms of x-linking.

|   | | Control | Vitamin | Esacure |
|---|---|---|---|---|
| 1 | Untreated control | 103 ± 7.1 | 110 ± 4.6 | 101 ± 1.9 |
| 2 | Beta | 95 ± 16 | 99 ± 5.0 | 95 ± 10 |
| 3 | Heat | 51 ± 13 | 18 ± 2.1 | 28 ± 1.9 |
| 4 | UV | 101 ± 6.2 | 107 ± 5.9 | 98 ± 5.1 |
| 5 | Heat-Beta | 46 ± 3.6 | 32 ± 1.6 | 50 ± 4.3 |
| 6 | UV-Beta | 102 ± 3.7 | 109 ± 2.8 | 107 ± 6.0 |
| 7 | Heat-UV | 34 ± 0.7 | 25 ± 0.8 | 35 ± 1.6 |
| 8 | UV-Heat | 45 ± 2.4 | 33 ± 1.1 | 28 ± 1.0 |
| 9 | Heat-UV-Beta | 43 ± 1.5 | 34 ± 0.8 | 51 ± 2.4 |
| 10 | UV-Heat-Beta | 79 ± 15 | 4 ± 2.1 | 42 ± 1.2 |

A statistical analysis reveals significance of all factors except UV. It is interesting to note that despite the evidence of UV induced x-linking could be seen upon hydration in PBS-buffer, the BCA protein assay showed no significant effect of UV. However, cross-linking with heat treatment had a positive effect, whereas beta irradiation (sterilization) has a negative effect. Best cross-linking on gelatin is seen with Vitamin $B_2$ and C—primarily due to heat treatment. Acceptable degree of cross-linking after beta irradiation on gelatin with Vitamin $B_2$ and C Example 13

To follow-up on the obtained results mentioned in example 12 new experiments were done, where essentially new control fibers were processed with low temperatures in order to compare to the processing temperature of the fibers containing vitamin. In the first place the temperature was kept as low as possible when processing the fibers containing vitamin in order to avoid destruction of the thermo-sensitive vitamins.

Surprisingly, it was found that fibers with pure gelatin (no vitamin) could be cross-linked just as well as the fibers containing vitamin mentioned in example 12. Negative controls were produced of both vitamin containing fiber and pure fibers. With negative controls is meant fibers produced with a high temperature and deliberately fast dried by blowing air on the newly produced fibers on the collecting device. Data is shown below.

Table: Fibers were produced with either pure gelatin or with gelatin containing 1% Vitamin C and 1% vitamin B2 (% dry matter of final non woven). The gelatin was a aqueous solution containing 24% gelatin (weight percentage). Processing temperature is the temperature of the polymer solution. Post air drying is continuous blowing of air on the produced non-woven in order to dry it rapidly. Cross-linking before beta irradiation is done after heat-treating the non-wovens at 160° C. for 1 hour under vacuum. A BCA assay is used to quantify the percentage of uncross-linked protein; thus a number of 100 means that the sample is not cross-linked, whereas a lower number is quantifies degree of cross-linking. Cross-linking after beta irradiation are data obtained of the above mentioned treatment followed by beta irradiation of the sample with a dose of 25 kGy. 4 replicates of BCA assay was done and the result is given as average±standard deviation.

| | Processing temperature | Post air drying | Cross-linking before beta irradiation | Cross-linking after beta irradiation |
|---|---|---|---|---|
| Vitamin | 40 | yes | 58 ± 1.3 | 87 ± 2.9 |
| Vitamin | 42 | yes | 64 ± 13 | 76 ± 3.2 |
| Vitamin | 42 | yes | 79 ± 3.2 | 91 ± 2.1 |
| Vitamin | 40 | yes | 91 ± 4.4 | 105 ± 2.1 |
| Vitamin | 75 | no | 101 ± 3.3 | 102 ± 4.9 |
| Control | 52 | no | 22 ± 1.1 | 42 ± 2.9 |
| Control | 75 | no | 23 ± 1.4 | 48 ± 2.6 |
| Control | 44 | no | 22 ± 0.8 | 35 ± 1.9 |
| Control | 42 | yes | 87 ± 1.1 | 102 ± 1.4 |

By keeping a relatively high processing temperature of 75° C. when producing fibers containing vitamins (row 5), the cross-linking was poor. Vitamin fibers dried fast by the "Post air drying" treatment were significantly poorer cross-linked compared to similar fibers in example 12. On the other hand the table shows that non-woven of control fibers (of pure gelatin) could be cross-linked to a degree comparable with what was found on the vitamin fibers in example 12. By rapidly drying the control fibers processed at a low temperature (lowest rows in the table) the cross-linking was significantly decreased.

Example 14

Processing of gelatin fibers containing two different types of glucosamine glucans (GAG) was done using the same processing equipment as described in the previous example. Spinning solutions were prepared from a 300 bloom porcine gelatin from Gelita. Aqueous solutions of gelatin was prepared 24% concentration. After dissolving the gelatin GAG's were mixed in. The dry matter content of GAG is 1% relative to the gelatin dry matter content. A spinning solution was prepared using either dermatan sulphate or chondroitin sulphate as GAG. The temperature of the processing air was 80° C., hence the temperature of the leaving spinning solution was 80° C., but the temperature of the rest of the setup was kept at 60° C. Cross-linked samples were produced by heat treatment for 1 hour at 160° C. under vacuum.

The amount of sulphated GAG content together with the gelatin fibers can be measured using the dimethylmethylen blue (DMMB) assay by an increase in OD 525 nm. The DMMB colour solution was prepared according to Farndale et al. (Biochimica et Biophysica Acta 883:173-177, 1986). Briefly, 16 mg 1,9 dimethylmethylene blue was dissolved in 1 L of water containing 3.04 g glycine, 2.37 g NaCl and 95 ml 0.1 M HCl, pH 3.0. Release of GAG from the cross-linked and non-cross-linked gelatin fibers+/−GAGs was measured by placing 6 mm biopsies of each type in duplicates in a 48 well plate. Two hundred μl of DMMB solution were poured over the scaffolds corresponding to the amount necessary to cover the scaffolds. Five minutes later 100 μl of the colour solution from the wells were transferred to a 96 well plate and measured at 525 nm. A Synergy™ HT Multi-Detection Microplate Reader from Bio-Tek was used.

Figure 9:
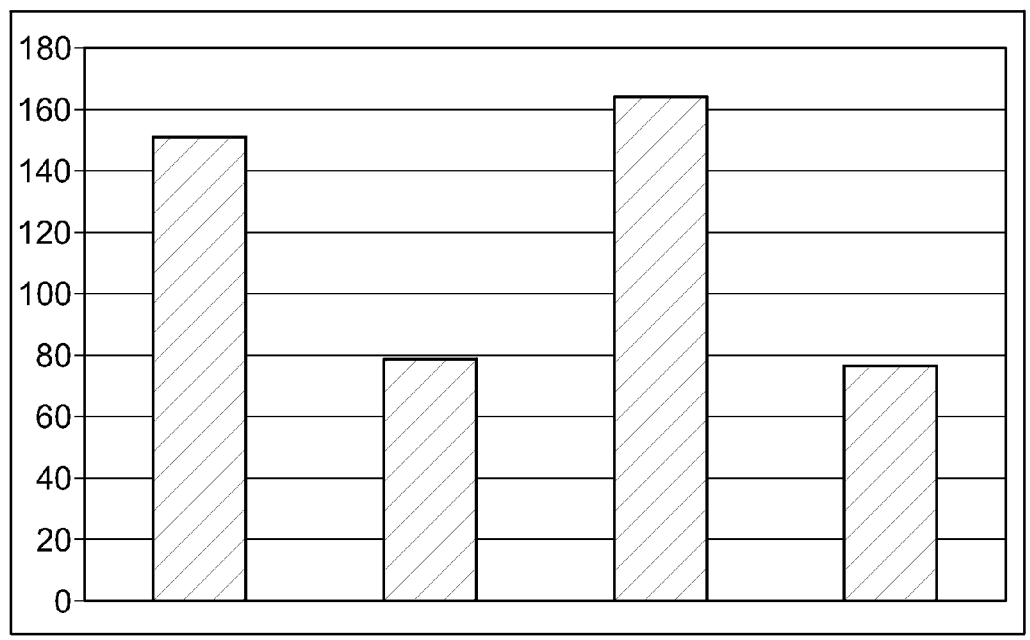

The result of the study showed an immediately release of GAG into the solution from the non cross-linked gelatin fibers containing both types of GAG whereas the cross-linked gelatin fibers containing the GAGs and the gelatin fibers without additives were coloured up without colouring the surrounding solution (FIG. 9). This means that the heat cross-linking not only cross-links the gelatin fibers but also somehow cross-links the GAGs into the structure.

Evaluation of the growth of fibroblasts on the cross-linked gelatin fibers+/−GAGs, biopsies were punched out of each type of the scaffolds and seeded with primary human fibroblasts (passage 4) on the surface with a density of 2.5×10⁴ cells/cm² in a small volume of growth medium (10% FCS in DMEM) containing antibiotics (penicillin, streptomycin and Amphotericin B). The scaffolds were incubated at 37° C. at 5% $CO_2$ before additional growth medium was added. Evaluation of the cells attachment, morphology, growth and population of the scaffold were performed on day 1, 3 and 7 by staining the cells with neutral red followed by evaluation using an Leica DMIRE2 inverted microscope fitted with a Evolution MP cooled colour camera (Media Cybernetics). Digital images were taken using Image Pro Plus 5.1 software (Media Cybernetics).

The fibroblasts were growing with spindle-shaped morphology on all three types of gelatin fiber scaffolds (pure gelatin fibers and the two gelatin fiber scaffolds containing two different GAGs) and an increasing in cell number was seen from day 1 and until day 7. The most predominant difference between the different types of scaffolds was that the cells were contracting them in different ways. The gelatin fibers containing CS increased in size whereas a contraction by the cells was seen in the gelatin fibers containing DS. The pure gelatin fiber scaffold were somewhere in between. The effect was happening somewhere between day 3 and day 7 and indicates that even through the GAGs are cross-linked into the gelatin fibers the GAGs are nevertheless accessible to the cells.

Example 15

Abstract

The effect of 3 different poly(carboxylic acids) (CMC, poly(acrylic acid), and pectin) and of pH on the dehydrothermal crosslinking of gelatin is examined. The presence of polycarboxylic acids give superior crosslinking compared to plain gelatin when the pH is ≤7 and when the concentration of polycarboxylic acid is ~9%. Polyacrylic acid is a better crosslinker than either CMC or pectin, and has an effect at the lower concentrations of 1 and 5%.

Materials and Methods:
Freeze Dryer
Gelatin Gelita SG 724-8 300 bloom from pig
CMC, Hercules Blanose 12M31P lot 80357
Pectin, Pomosin LM-12CG-Z
Poly(acrylic acid), BASF Sokalan CP10S, 45% aqueous solution
pH-meter
BCA-assay (Sigma BCA-1)
Dilute HCl (approx 0.5%)—for adjustment of pH
Dilute NaOH (approx 0.5%)—for adjustment of pH
Phosphate buffer: 7.2 g NaCl+1.48 g Na2HPO4+0.43 g KH2PO4 diluted to 1 L with water
G: 80 g gelatin is dissolved in hot water to 4 L (2% w/v)
PAA: 8.89 g Sokalan 45% is dissolved to 200 mL (2% w/v)
CMC: 6 g CMC is dissolved in hot water to 300 mL (2% w/v)
P: 6 g pectin is dissolved in hot water to 300 mL (2% w/v)
0% poly(carboxylic acid): 75 ml G is adjusted to pH (4, 5, 6, 7, 8, 9), The volume is adjusted to 100 ml, the solution is poured in an aluminium mold (ø50 mm), placed at 5° C. until the solution has gelled, and is frozen at −20° C., and then freeze-dried.
1% poly(carboxylic acid): To 75 ml G is added 0.75 ml of PAA, CMC or P with stirring, and pH is adjusted to (6, 7, 8, 9). The volume is adjusted to 100 ml, the solution is poured in an aluminium mold (ø50 mm), placed at 5° C. until the solution has gelled, and is frozen at −20° C., and then freeze-dried.
4.8% poly(carboxylic acid): To 75 ml G is added 3.75 ml of PAA, CMC or P with stirring, and pH is adjusted to (6, 7, 8, 9). The volume is adjusted to 100 ml, the solution is poured in an aluminium mold (ø50 mm), placed at 5° C. until the solution has gelled, and is frozen at −20° C., and then freeze-dried.
9.1% poly(carboxylic acid): To 75 ml G is added 7.5 ml of PAA, CMC or P with stirring, and pH is adjusted to (6, 7, 8, 9). The volume is adjusted to 100 ml, the solution is poured in an aluminium mold (ø50 mm), placed at 5° C. until the solution has gelled, and is frozen at −20° C., and then freeze-dried.

Cross-Linking:

The freeze-dried porous structures are placed in a vacuum oven (160° C./<0.1T) for 1 h.

The table below shows the design of the experiment (all the volumes are adjusted to 100 ml with water after adjustment of the pH):

|    | Konc | pH | poly-COOH | mL Gelatin | mL PAA | mL CMC | mL P |
|----|------|----|-----------|------------|--------|--------|------|
| 1  | 0    | 4  |           | 75         |        |        |      |
| 2  | 0    | 5  |           | 75         |        |        |      |
| 3  | 0    | 6  |           | 75         |        |        |      |
| 4  | 0    | 7  |           | 75         |        |        |      |
| 5  | 0    | 8  |           | 75         |        |        |      |
| 6  | 0    | 9  |           | 75         |        |        |      |
| 7  | 1    | 6  | PAA       | 75         | 0.75   |        |      |
| 8  | 1    | 7  | PAA       | 75         | 0.75   |        |      |
| 9  | 1    | 8  | PAA       | 75         | 0.75   |        |      |
| 10 | 1    | 9  | PAA       | 75         | 0.75   |        |      |
| 11 | 1    | 6  | CMC       | 75         |        | 0.75   |      |
| 12 | 1    | 7  | CMC       | 75         |        | 0.75   |      |
| 13 | 1    | 8  | CMC       | 75         |        | 0.75   |      |
| 14 | 1    | 9  | CMC       | 75         |        | 0.75   |      |
| 15 | 1    | 6  | P         | 75         |        |        | 0.75 |
| 16 | 1    | 7  | P         | 75         |        |        | 0.75 |
| 17 | 1    | 8  | P         | 75         |        |        | 0.75 |
| 18 | 1    | 9  | P         | 75         |        |        | 0.75 |
| 19 | 4.8  | 6  | PAA       | 75         | 3.75   |        |      |
| 20 | 4.8  | 7  | PAA       | 75         | 3.75   |        |      |
| 21 | 4.8  | 8  | PAA       | 75         | 3.75   |        |      |
| 22 | 4.8  | 9  | PAA       | 75         | 3.75   |        |      |
| 23 | 4.8  | 6  | CMC       | 75         |        | 3.75   |      |
| 24 | 4.8  | 7  | CMC       | 75         |        | 3.75   |      |
| 25 | 4.8  | 8  | CMC       | 75         |        | 3.75   |      |
| 26 | 4.8  | 9  | CMC       | 75         |        | 3.75   |      |
| 27 | 4.8  | 6  | P         | 75         |        |        | 3.75 |
| 28 | 4.8  | 7  | P         | 75         |        |        | 3.75 |
| 29 | 4.8  | 8  | P         | 75         |        |        | 3.75 |
| 30 | 4.8  | 9  | P         | 75         |        |        | 3.75 |
| 31 | 9.1  | 6  | PAA       | 75         | 7.5    |        |      |
| 32 | 9.1  | 7  | PAA       | 75         | 7.5    |        |      |
| 33 | 9.1  | 8  | PAA       | 75         | 7.5    |        |      |
| 34 | 9.1  | 9  | PAA       | 75         | 7.5    |        |      |
| 35 | 9.1  | 6  | CMC       | 75         |        | 7.5    |      |
| 36 | 9.1  | 7  | CMC       | 75         |        | 7.5    |      |
| 37 | 9.1  | 8  | CMC       | 75         |        | 7.5    |      |
| 38 | 9.1  | 9  | CMC       | 75         |        | 7.5    |      |
| 39 | 9.1  | 6  | P         | 75         |        |        | 7.5  |
| 40 | 9.1  | 7  | P         | 75         |        |        | 7.5  |
| 41 | 9.1  | 8  | P         | 75         |        |        | 7.5  |
| 42 | 9.1  | 9  | P         | 75         |        |        | 7.5  |

BCA-assay: 2-4 mg scaffold is weighed to a 4 mL screw-cap vial. 3 mL buffer is added, the vial is closed and placed in a water bath at 60° C. for 1 h, and then shaken at room temperature overnight. The samples are filtered, and soluble gelatin is determined spectrophotometrically with a BCA-assay (Sigma BCA-1).

Results and Discussion:

In all the graphs (FIGS. 10, 11 and 12), the x-axis is pH and the y-axis % soluble gelatin. A lower % soluble gelatin equals a higher degree of cross-linking. These values are compared to gelatin without additives at different pH (FIG. 13): There seems to be little influence of the pH on the degree of cross-linking of pure gelatin. For the polycarboxylic acids, the PAA gives the strongest effects and the cross-linking seems to be best at the lower pH-values (6-7). Only PAA give an enhanced cross-linking at the lower concentrations, while pectin and CMC only have an effect at the high concentration (9.1%).

Conclusion:

The effect of 3 different poly(carboxylic acids) (CMC, poly(acrylic acid) and pectin) and pH on the dehydro-thermal cross-linking of gelatin is examined. The presence of polycarboxylic acids give superior cross-linking compared to plain gelatin when the pH is ≤7 and when the concentration of polycarboxylic acid is ~9%. Polyacrylic acid is a better crosslinker than either CMC or pectin, and has an effect at the lower concentrations of 1 and 5%.

Example 16

Viscosities at different temperatures were measured on aqueous solutions of porcine gelatin from Gelita, bloom 300, using a Brookfield DV-II+ viscometer. Concentration of gelatin was from 15% to 35% (weight percentage). Included was also a solution made of 30% gelatin, 65% water, and 5% n-propanol (weight percentages). The following table summarizes the obtained results:

TABLE 3

Viscosities in mPas measured with Brookfield viscometer.

|  | 40° C. | 50° C. | 60° C. | 70° C. |
| --- | --- | --- | --- | --- |
| 15% gelatin | 73 | 55 | 42 | 33 |
| 20% gelatin | 302 | 167 | 126 | 101 |
| 25% gelatin | 1566 | 525 | 397 | 320 |
| 30% gelatin | 18956 | 1572 | 1164 | 936 |
| 30% gelatin + 5% n-propanol | 3407 | n.d. | 1221 | 885 |
| 35% gelatin | >1000000 | 7378 | 3199 | 2120 |

The conclusion is that viscosity increases with concentration of gelatin, but decreases with higher temperature. Addition of alcohol lowers the viscosity close to the sol-gel transition state temperature. Weak fiber formation properties are related to low viscosity. Difficulties with processing due to too high viscosity may be overcome by raising processing temperature.

Example 17

Spinning solution were prepared by dissolving porcine gelatin from Gelita with bloom 300 in water to a concentration of 25% with either 9.1% of carboxylmethyl cellulose, CMC, type 12 M31P from Hercules or 9.1% polyacrylic acid, PAA, (Sokalan CP 10S from BASF) (weight percentages).

The dissolved gelatin solution was transferred to a can (1 Liter), which fit a small lab-size bulk melter (example 4). The bulk melter heats only the upper surface of the material in the can, which then becomes viscous and therefore can be pumped to a dispensing unit, mounted hereto. The dispensing unit is a CF-200 Controlled Fiberization Gun provided from Nordson Corp, equipped with a nozzle with 0.012 inch orifice and 6 air holes. The temperature of the bulk melter can be controlled in its different parts. The temperature of the gun can be controlled and the temperature and rate of the air is controlled. The pump was set at 1 (CMC) and 2 (PAA). Air pressure was 1.1 (CMC) and 1.7 (PAA), and temperature of air was 51° C. (PAA), however varied from 61-74° C. when processing the PAA spinning solution. A fibrous non-woven structure could be obtained by collecting on the outer surface of a rotating cylinder. The rotation axis was horizontal. By using a X-Y table the rotating cylinder was moved from side to side along the horizontal rotation axis. Distance from nozzle to collecting surface was 30 cm. The diameter of the rotating cylinder was 30 cm. The collecting device was placed under the nozzle such that the extruded fibers hit the rotating cylinder almost tangentially. Rotational direction was same direction as the extrusion direction (not against). When a constant rate of the movements of the collecting device was maintained and the rate of fiber output was kept constant it was possible to create a non-woven sheet, which has a uniform appearance.

In order to cross-link the resulting non-wovens samples were heat treated for 1 hour at 160° C. under vacuum. Sterilization was done by beta irradiation of 25 kGy. Quantification of degree of cross-linking was done by BCA assay as described in previous examples. The following results were obtained:

|  | 0 kGy | 25kGy |
| --- | --- | --- |
| Gelatine 24% | 24.16 ± 1.73 | 35.62 ± 1.85 |
| Gelatine 25%, 9.1% CMC | 19.86 ± 0.84 | 21.55 ± 0.74 |
| Gelatin 25%, 9.1% PAA | 18.51 ± 1.62 | 16.33 ± 2.10 |

The conclusion is that the added polycarboxylic acids are effective cross-linkers and that the cross-linking effect resists beta irradiation at the given doses.

Figures

FIG. 1: Labscale production of gelatin non-woven using the inside of a rotating cylinder as the collecting device.

FIG. 2: Gelatin non-woven made from 30% aqueous gelatin. Light microscopy 10× magnification. Scale bar is 50 μm.

FIG. 3: Gelatin non-woven with UBM particles. Scale bar is 100 μm.

FIG. 4: Picture showing examples of nozzles used to make gelatin non-woven. The orifice is found on the top of the raised center part. There are either 6 or 12 air holes in a circle around the orifice.

FIG. 5: Photograph of gelatin non-woven showing its macroscopic appearance.

FIG. 6: Gelatin control 10× magnification. Scalebar 50 μm

FIG. 7: Gelatin vitamin 10× magnification. Scalebar 50 μm

FIG. 8: Gelatin Esacure 10× magnification. Scalebar 50 μm

FIG. 9: Release of two different types of GAG from cross-linked and non-cross-linked gelatin fibers. The figure shows release of GAG from gelatin fibers, on the y-axis, the % of control; on the x-axis the Gelatin with 1% CS (first bar); Gelatin with 1% CS cross-linked (second bar); Gelatin with 1% DS (third bar); and Gelatin with 1% DS cross-linked (forth bar).

Figure 10A:
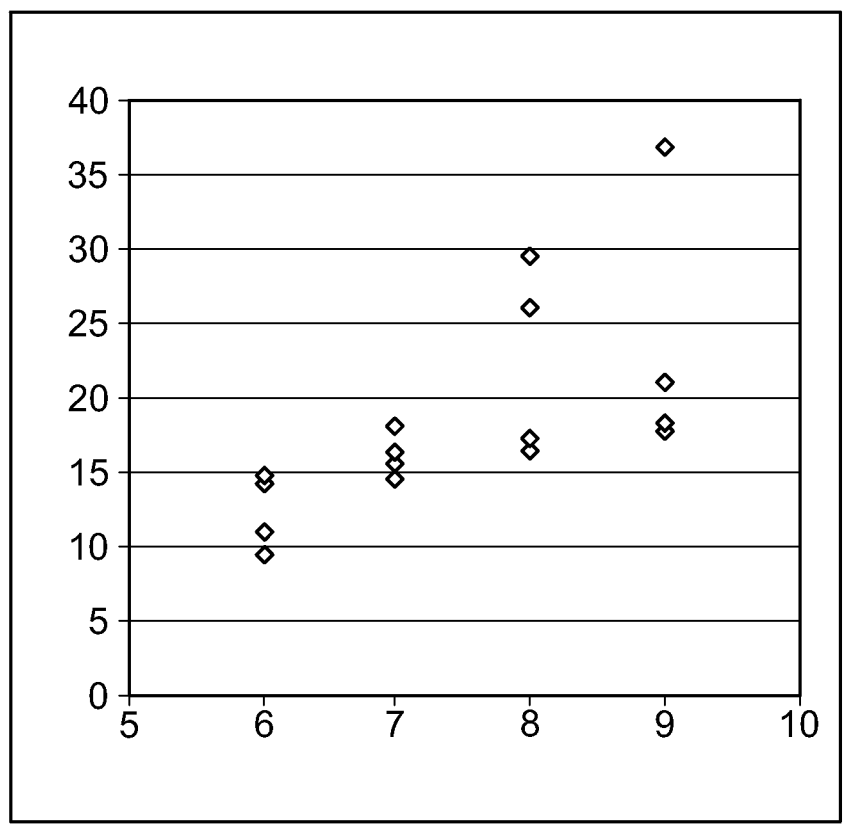

FIG. 10A: The x-axis is pH and the y-axis % soluble gelatin. A lower % soluble gelatin equals a higher degree of crosslinking. 1% PAA was used.

Figure 10B:
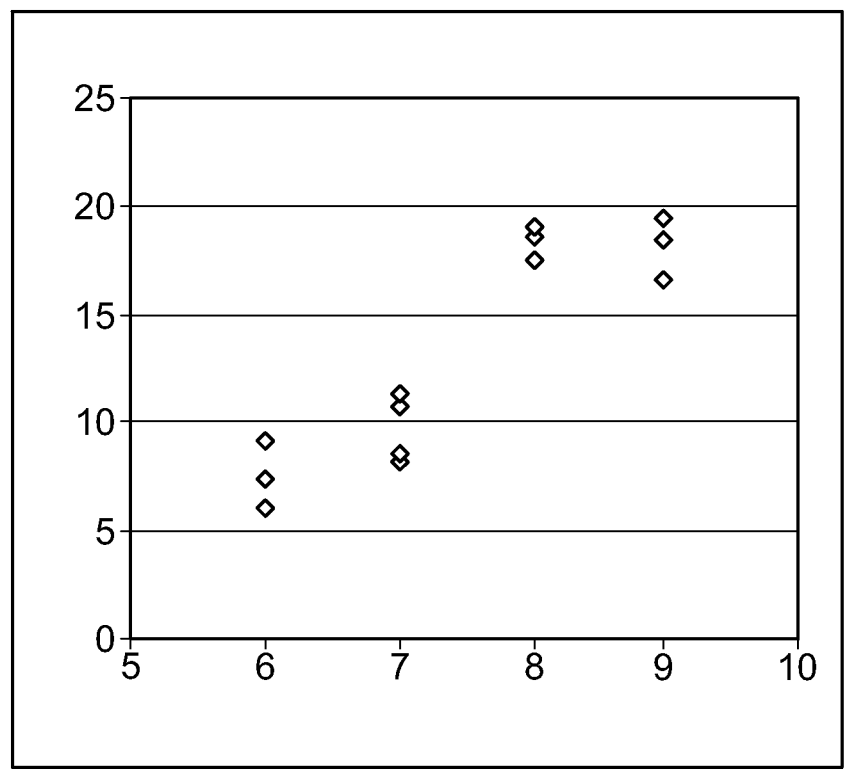

FIG. 10B: The x-axis is pH and the y-axis % soluble gelatin. A lower % soluble gelatin equals a higher degree of crosslinking. 1% CMC was used.

Figure 10C:
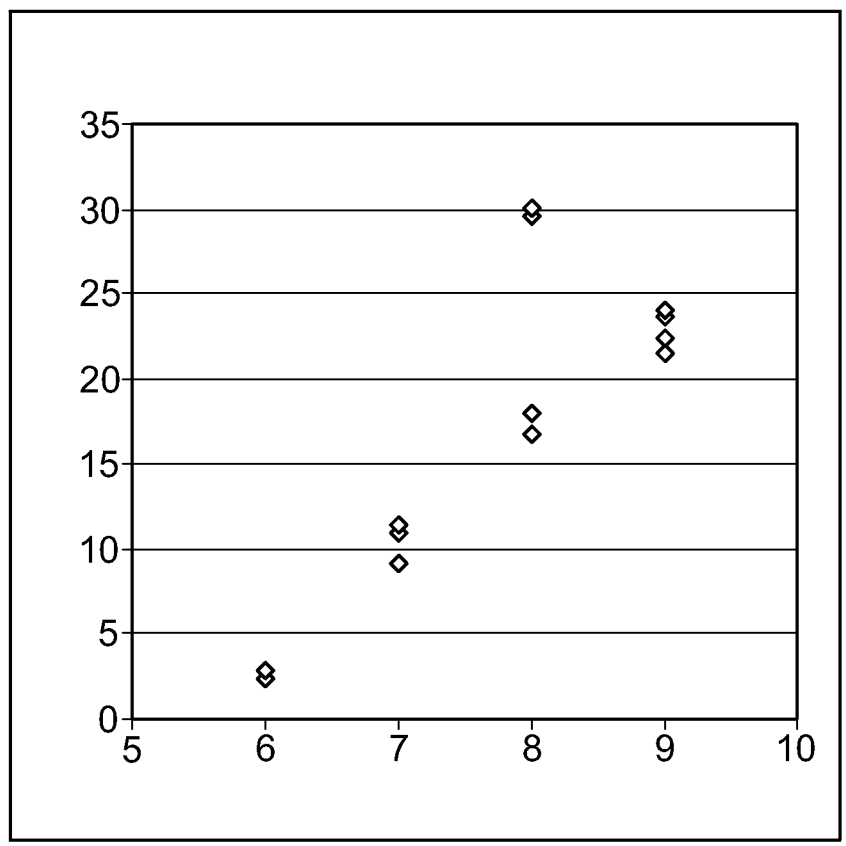

FIG. 10C: The x-axis is pH and the y-axis % soluble gelatin. A lower % soluble gelatin equals a higher degree of crosslinking. 1% pectin was used.

Figure 11A:
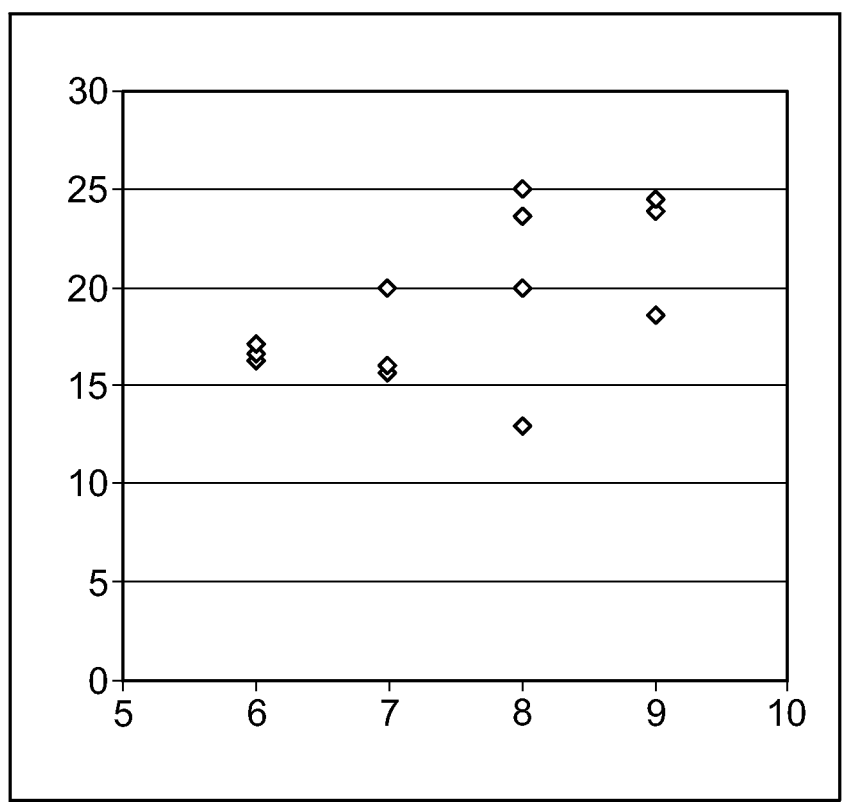

FIG. 11A: The x-axis is pH and the y-axis % soluble gelatin. A lower % soluble gelatin equals a higher degree of crosslinking. 4.8% PAA was used.

Figure 11B:
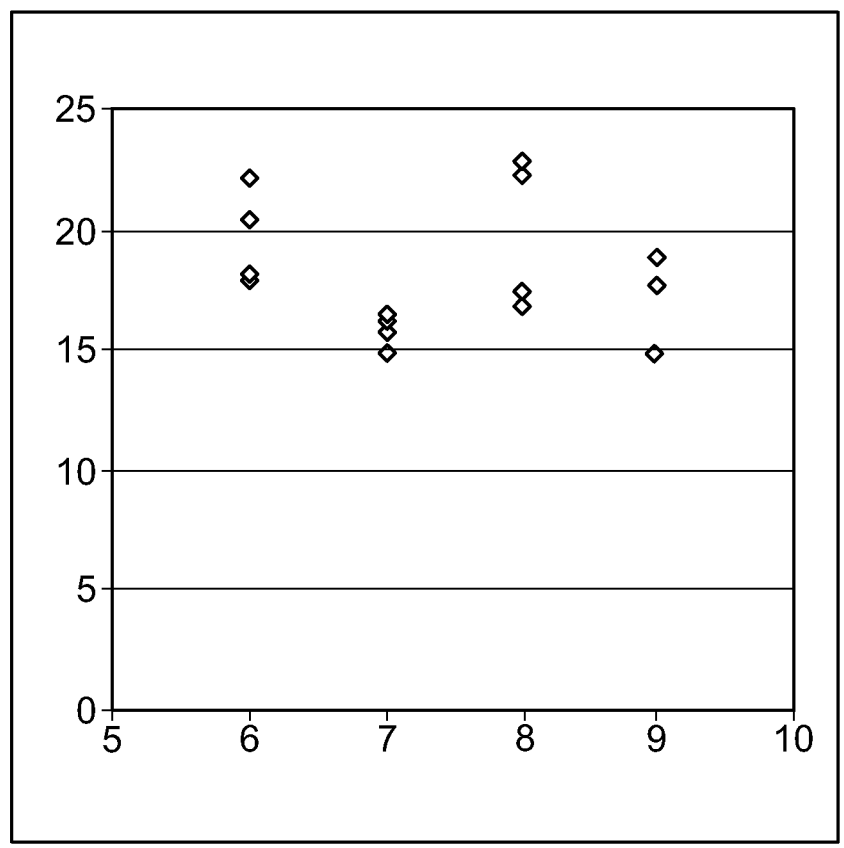

FIG. 11B: The x-axis is pH and the y-axis % soluble gelatin. A lower % soluble gelatin equals a higher degree of crosslinking. 4.8% CMC was used.

Figure 11C:
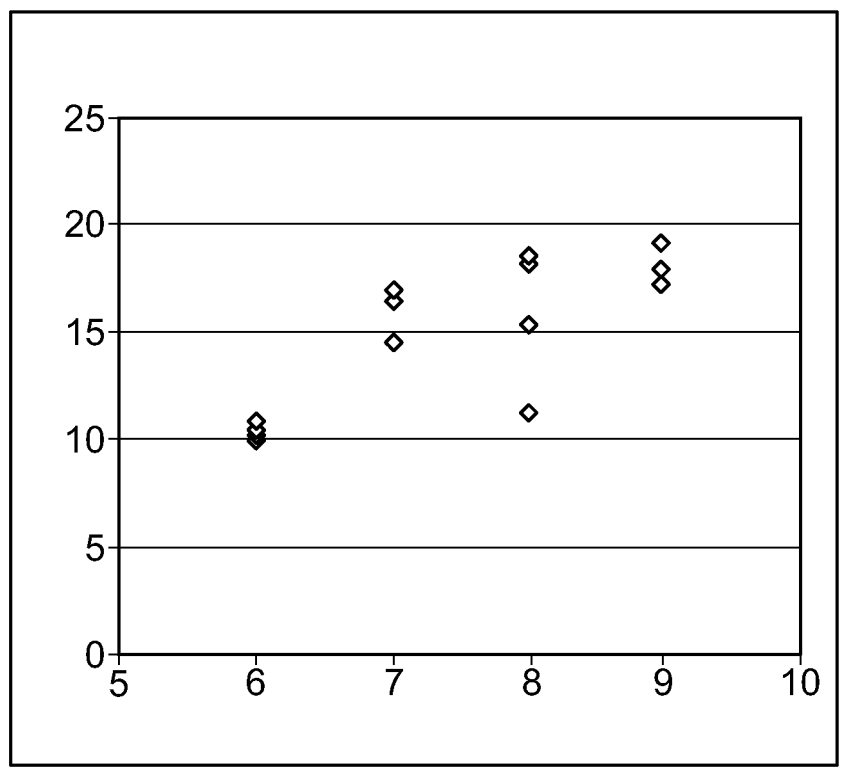

FIG. 11C: The x-axis is pH and the y-axis % soluble gelatin. A lower % soluble gelatin equals a higher degree of crosslinking. 4.8% pectin was used.

Figure 12A:
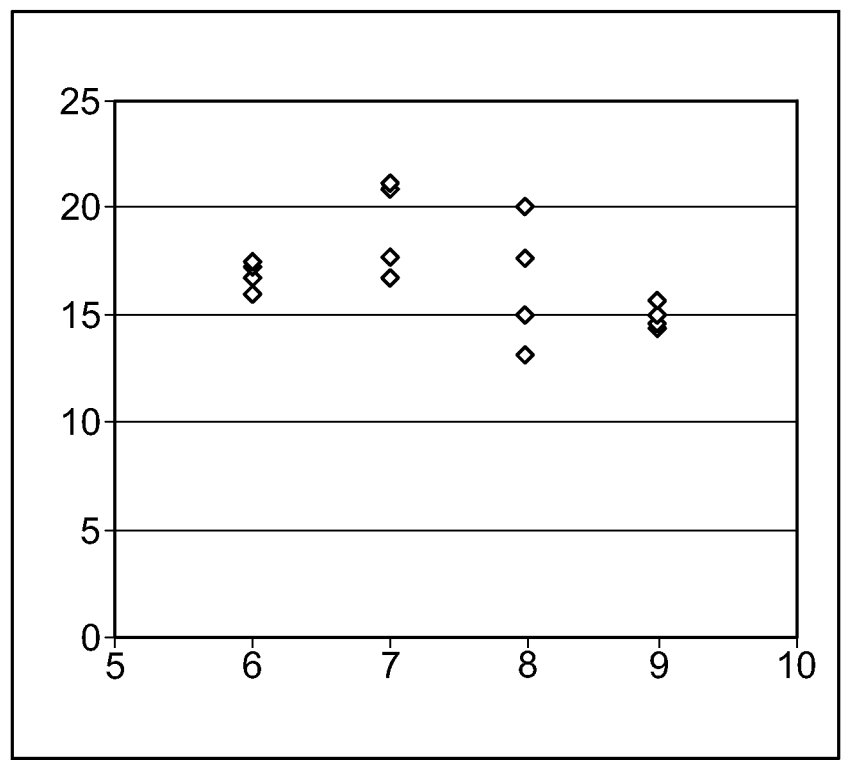

FIG. 12A: the x-axis is pH and the y-axis % soluble gelatin. A lower % soluble gelatin equals a higher degree of crosslinking. 9.1% PAA was used.

Figure 12B:
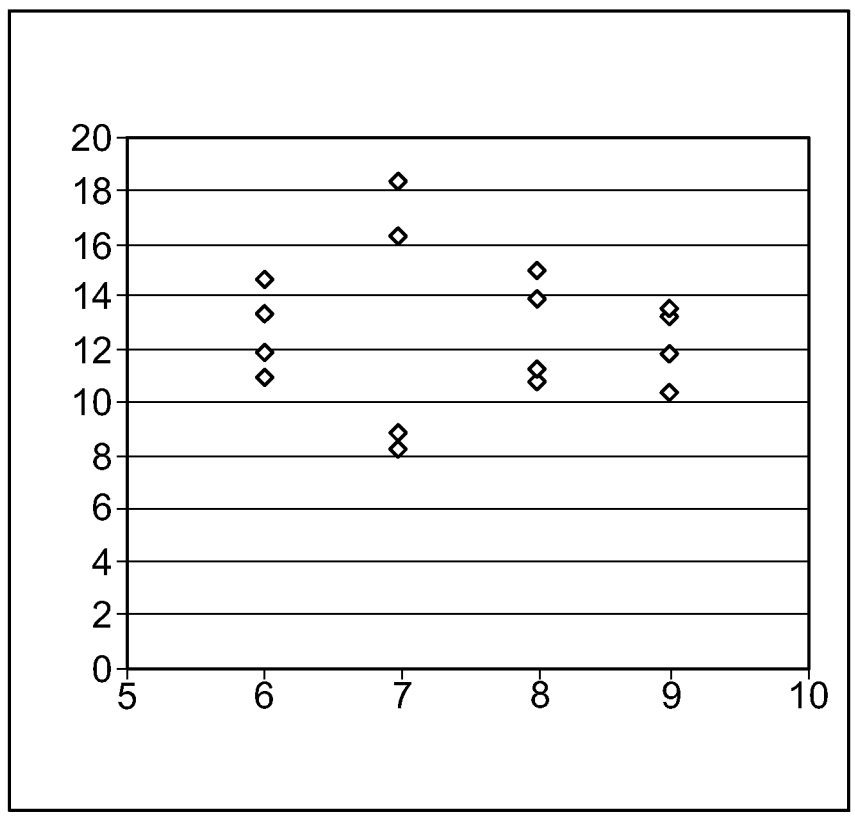

FIG. 12B: the x-axis is pH and the y-axis % soluble gelatin. A lower % soluble gelatin equals a higher degree of crosslinking. 9.1% CMC was used.

Figure 12C:
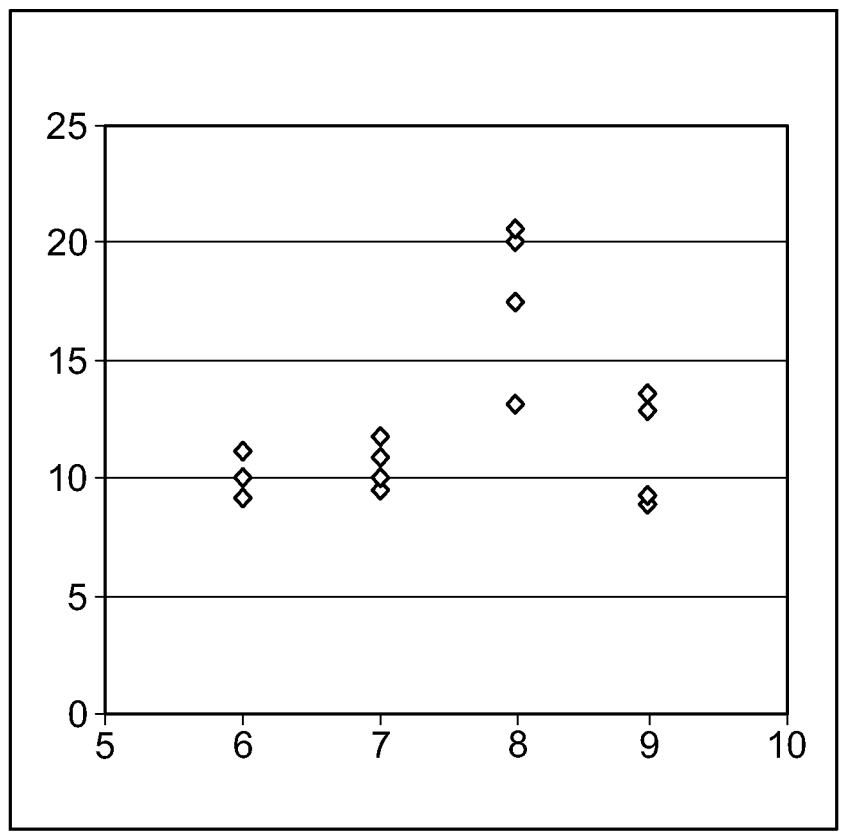

FIG. 12C: the x-axis is pH and the y-axis % soluble gelatin. A lower % soluble gelatin equals a higher degree of crosslinking. 9.1% pectin was used.

Figure 13:
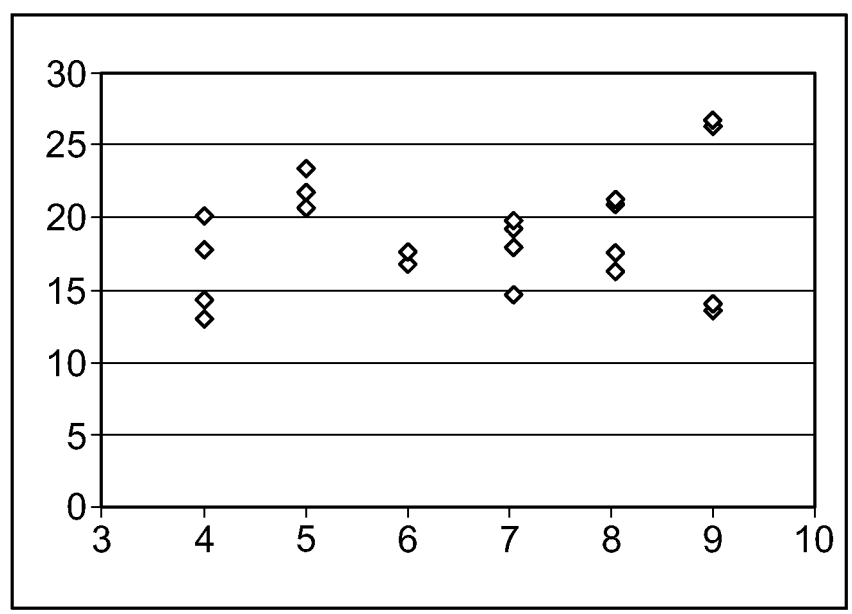

FIG. 13: The x-axis is pH and the y-axis % soluble gelatin, for gelatin without additives at different pH.

The invention claimed is:

1. A method of producing gelatin fibers containing glycosaminoglycans comprising the steps of:
   (a) ejecting an aqueous alcoholic solution of gelatin and glycosaminoglycans through a nozzle to form gelatin fibers containing glycosaminoglycans (GAGs), wherein the aqueous alcoholic solution includes less than 25% low molecular weight alcohol; while
   (b) emitting pressurized air from air jet bores into the gelatin fibers containing the GAGs exiting the nozzle to attenuate or stretch the gelatin fiber containing the GAGs; while
   (c) collecting the gelatin fibers containing the GAGs on a collecting device.

2. The method according to claim 1, wherein the viscosity of the aqueous solution of gelatin is between 1000 and 2000 mPas at a processing temperature of 40° C.

3. The method according to claim 1, wherein the nozzle has an orifice between 0.008 inch and 0.050 inch.

4. The method according to claim 1, wherein the aqueous solution comprises less than 10% low molecular alcohol.

5. The method according to claim 1, wherein the aqueous solution comprises less than 1% low molecular alcohol.

6. The method according to claim 1, wherein the low molecular weight alcohol is selected from the group consisting of methanol, ethanol, 1-propanol, 2-propanol, and 1-butanol.

7. The method according to claim 1, wherein the collection takes place in parallel to the ejection.

8. The method according to claim 1, further comprising the step of forming a non-woven structure from the gelatin fibers containing GAGs as they are collected.

9. The method according to claim 1, further comprising the step of allowing the gelatin fibers containing GAGs to gel prior to drying.

10. The method according to claim 1, wherein the aqueous gelatin solution further comprises a polycarboxylic acid.

* * * * *